United States Patent
Basset et al.

(10) Patent No.: US 11,952,335 B2
(45) Date of Patent: Apr. 9, 2024

(54) PROCESS FOR PREPARING 1-INDANONE COMPOUNDS BY INTRAMOLECULAR FRIEDEL-CRAFTS REACTION OF ALPHA,ALPHA-DIALKYLMALONATE DERIVATIVES

(71) Applicant: FIRMENICH SA, Satigny (CH)

(72) Inventors: Jean-François Basset, Satigny (CH); Philippe Dupau, Satigny (CH); Iris Magpantay, Satigny (CH); Murielle Haldimann Sanchez, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 17/761,016

(22) PCT Filed: Dec. 8, 2020

(86) PCT No.: PCT/EP2020/085066
§ 371 (c)(1),
(2) Date: Mar. 16, 2022

(87) PCT Pub. No.: WO2021/116099
PCT Pub. Date: Jun. 17, 2021

(65) Prior Publication Data
US 2022/0356143 A1    Nov. 10, 2022

(30) Foreign Application Priority Data
Dec. 13, 2019   (EP) .................................. 19216279

(51) Int. Cl.
*C07C 61/13* (2006.01)
*C07C 57/30* (2006.01)
*C07C 67/313* (2006.01)

(52) U.S. Cl.
CPC .............. *C07C 61/13* (2013.01); *C07C 57/30* (2013.01); *C07C 67/313* (2013.01); *C07C 2602/08* (2017.05)

(58) Field of Classification Search
CPC ....... C07C 61/13; C07C 57/30; C07C 67/313; C07C 2602/08
See application file for complete search history.

(56) References Cited

U.S. PATENT DOCUMENTS

| | | | |
|---|---|---|---|
| 5,708,018 A | * | 1/1998 | Haadsma-Svensson ..................... C07C 311/08 514/408 |
| 6,323,173 B1 | | 11/2001 | Winter et al. |
| 2010/0222345 A1 | * | 9/2010 | Diaz .................... C07D 471/04 514/307 |

FOREIGN PATENT DOCUMENTS

| | | | | |
|---|---|---|---|---|
| CN | 108324716 A | | 7/2018 | |
| EP | 1022265 A1 | | 7/2000 | |
| EP | 1508562 | * | 2/2005 | |
| EP | 1508562 A1 | | 2/2005 | |
| WO | 2019092056 A1 | | 5/2019 | |
| WO | WO 2019/092056 | * | 6/2019 | ........... C07C 47/453 |

OTHER PUBLICATIONS

Falk, H., et al., Darstellung, absolute Konfiguration und optische Reinheit von 2,2'-Spiro-biindan-1,1'-dion, Monatschefte fur - Chemie , 105, pp. 574-597 (Year: 1974).*

Mishra, C. R., Experiments towards he syntehsis of iludalic acid: synthesis of 2,2-dimethyl-4-hydroxy-5-formylindane, Journal of the Institute of Chemists, (India), 62(2), pp. 85-89, 1 page abstract (Year: 1990).*

International Search Report and Written Opinion for related International Patent Application No. PCT/EP2020/085066, dated Feb. 17, 2021, 12 pages.

H. Falk et al: "Darstellung, absolute Konfiguration and optische Reinheit von 2,2'-spiro-biindan-1,1'-dion", Monatshefte Fur Chemie, vol. 105, 1974, pp. 574-597. Cited in ISR for related PCT/EP2020/085066; no English translation available.

Cui D-M et al: "Synthesis of 1-indanones by intramolecular Friedel-Crafts reaction of 3-arylpropionic acids catalyzed by Tb(0Tf)"3", Tetrahedron Letters, vol. 45, No. 8, Feb. 16, 2004, pp. 1741-1745.

Cazetta et al: "Trichosporon cutaneum-promoted deracemization of (+/−)-2-hydroxindan-l-one: a mechanistic study", Tetrahedron Asymmetry, vol. 18, No. 17, Oct. 2007, pp. 2030-2036.

Winter et al: "Synthesis and Odor Properties of Substituted Indane-2-carboxaldehydes. Discovery of a New Floral (Muguet) Fragrance Alcohol", Helvetica Chimica Acta, vol. 88, 2005, pp. 3118-3127.

* cited by examiner

*Primary Examiner* — Yate' K Cutliff
(74) *Attorney, Agent, or Firm* — Armstrong Teasdale LLP

(57) ABSTRACT

Described herein are valuable new chemical intermediates for producing perfuming ingredients, and a process for producing compound of formula (I).

15 Claims, No Drawings

PROCESS FOR PREPARING 1-INDANONE COMPOUNDS BY INTRAMOLECULAR FRIEDEL-CRAFTS REACTION OF ALPHA,ALPHA-DIALKYLMALONATE DERIVATIVES

CROSS-REFERENCE TO RELATED APPLICATIONS

This application is a U.S. National Phase Application of International Patent Application No. PCT/EP2020/085066, filed Dec. 8, 2020, which claims priority to European Patent Application No. 19216279.0, filed Dec. 13, 2019, each of which is hereby incorporated by reference herein in its entirety.

TECHNICAL FIELD

The present invention relates to the field of perfumery. More particularly, it concerns valuable new chemical intermediates for producing perfuming ingredients. Moreover, the present invention comprises also a process for producing compound of formula (I).

BACKGROUND OF THE INVENTION

Compounds of formula (IV) are highly valuable perfumery ingredients and in particular (2,5-dimethyl-2,3-dihydro-1H-inden-2-yl)methanol which has been reported in EP 1022265 and also known as Lilyflore® (origin: Firmenich SA). The process to obtain those type of 2,2-disubstituted-2,3-dihydro-1H-indene derivatives passes generally through a cyclisation step to obtain 2-methyl-2,3-dihydro-1H-inden-1-one derivatives which then react with toxic and difficult to handle reagents such as formaldehyde or lithium diisopropyl amide. The direct cyclisation to obtain compound of formula (I) has never been reported. In addition, compounds of formula (IV) being products of industrial interest, new process leading to increase of yield and/or productivity is always highly sought.

So, there is a need to develop a more straightforward approach toward compounds of formula (I) using reagents which may be safer and more easily used at a larger scale while improving yield.

The present invention allows obtaining compound of formula (I) starting from compound of formula (II) under Friedel-Crafts conditions. Such a Friedel-Craft cyclisation starting from a tetrasubstituted substrate such as compound of formula (II) without the necessity to first form an acyl chloride has been reported only one time in *Monatschefte für Chemie*, 1974, 574 wherein the cyclisation of 2,2-dibenzyl-3-ethoxy-3-oxopropanoic acid leads meanly to the formation of side product.

SUMMARY OF THE INVENTION

The invention relates to a novel process allowing the preparation of compound of formula (I) starting from compound of formula (II) opening a new route toward compound of formula (IV).

So, the first object of the present invention is a process for the preparation of a compound of formula

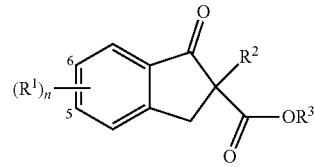

in the form of any one of its stereoisomers or a mixture thereof, and wherein n is an integer between 0 and 2, each $R^1$, independently from each other, represents a substituent of the aromatic ring and is a $C_{1-6}$ alkyl group, a $C_{2-6}$ alkenyl group or a $C_{1-6}$ alkoxy group; $R^2$ represents a $C_{1-3}$ alkyl group; and $R^3$ represents a hydrogen atom, a $C_{1-6}$ alkyl group or a $C_{2-6}$ alkenyl group;

comprising the cyclisation of a compound of the formula (II)

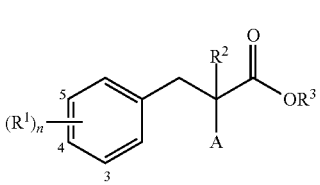

in the form of any one of its stereoisomers or a mixture thereof, and wherein n, $R^1$, $R^2$ and $R^3$ have the same meaning as defined in formula (I); and A represents a $C(O)OC(O)R^4$ group, a $C(O)Cl$ group or a COOH group wherein $R^4$ represents a $C_{1-6}$ alkyl group substituted by one or more chlorine or fluorine atoms;

in a presence of a Friedel-Crafts acylation reagent.

A Second object of the present invention is a compound of formula

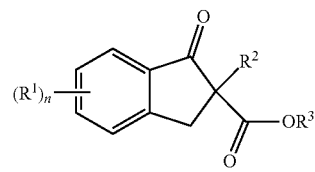

in the form of any one of its stereoisomers or a mixture thereof, and wherein n is an integer between 0 and 2, each $R^1$, independently from each other, represents a substituent of the aromatic ring and is a $C_{1-6}$ alkyl group, a $C_{2-6}$ alkenyl group or a $C_{1-6}$ alkoxy group; $R^2$ represents a $C_{1-3}$ alkyl group; and $R^3$ represents a hydrogen atom, a $C_{1-6}$ alkyl group or a $C_{2-6}$ alkenyl group; provided that 5-methoxy-2-methyl-1-oxo-2,3-dihydro-1H-indene-2-carboxylic acid, methyl 2-ethyl-5-methyl-1-oxo-2,3-dihydro-1H-indene-2-carboxylate, methyl 2-ethyl-6-methoxy-1-oxo-2,3-dihydro-1H-indene-2-carboxylate, ethyl 1-oxo-2-propyl-2,3-dihydro-1H-indene-2-carboxylate, methyl 2-ethyl-1-oxo-2,3-dihydro-1H-indene-2-carboxylate, methyl 2-isopropyl-1-oxo-2,3-dihydro-1H-indene-2-carboxylate, methyl 6-methoxy-1-oxo-2-propyl-2,3-dihydro-1H-indene-2-carboxylate, 2-methyl-1-oxo-2,3-dihydro-1H-indene-2-carboxylic acid, methyl 2-methyl-1-oxo-2,3-dihydro-1H-indene-2-carboxylate, ethyl 2-methyl-1-oxo-2,3-dihydro-1H-indene-2-carboxylate, allyl 2-methyl-1-oxo-2,3-dihydro-1H-indene-2-carboxylate, methyl 6-methoxy-2-methyl-1-oxo-2,3-dihydro-1H-indene-2-carboxylate, tert-butyl 2-methyl-1-oxo-2,3-dihydro-1H-indene-2-carboxylate, methyl 4-methoxy-2-methyl-1-oxo-2,3-dihydro-1H-indene-2-carboxylate, methyl 5,6-dimethoxy-2-methyl-1-oxo-2,3-dihydro-1H-indene-2-carboxylate, methyl 6-isobutyl-2-methyl-1-oxo-2,3-dihydro-1H-indene-2-carboxylate, ethyl 5-(tert-butyl)-2-methyl-1-oxo-2,3-dihydro-1H-indene-2-carboxylate, ethyl 2,5,7-trimethyl-1-oxo-2,3-dihydro-1H-indene-2-carboxylate and tert-butyl 5-methoxy-2-methyl-1-oxo-2,3-dihydro-1H-indene-2-carboxylate are excluded.

A third object of the present invention is a compound of formula

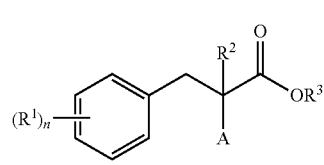

(II")

in the form of any one of its stereoisomers or a mixture thereof, and wherein n is an integer between 0 and 2, each $R^1$, independently from each other, represents a substituent of the aromatic ring and is a $C_{1-6}$ alkyl group, a $C_{2-6}$ alkenyl group or a $C_{1-6}$ alkoxy group; $R^2$ represents a $C_{1-3}$ alkyl group; $R^3$ represents a hydrogen atom, a $C_{1-6}$ alkyl group or a $C_{2-6}$ alkenyl group and A represents a C(O)Cl group; a C(O)OC(O)$R^5$ group, and $R^5$ represents a $C_{1-6}$ alkyl group provided that ethyl 3-chloro-2-(4-methoxy-3-methylbenzyl)-2-methyl-3-oxopropanoate is excluded.

DESCRIPTION OF THE INVENTION

It has now been surprisingly found that the perfuming ingredients reported in EP 1022265 can be obtained from a new class of precursors (or chemical intermediates), as defined herein below in formula (II), and that said new intermediates allow obtaining the corresponding perfuming ingredients reported in EP 1022265 with overall higher yield, compared to the methods known from the prior art. The invention's process is a Friedel-Craft reaction which have been largely reported on substrate without tetrasubstituted carbon in alpha position of the carbonyl group and/or on acid chloride. However, the preparation of acyl chloride request a supplementary step producing corrosive and toxic side-product. The high-yield cyclisation on a non-acid chloride substrate has only been reported on acid to form unsubstituted indanone. The present invention unexpectedly provides a straightforward access to compound of formula (I) in high yield while limiting even preventing the decarboxylation side reaction. In addition, the invention's process allows preventing the extra steps of formation of acyl chloride and/or the substitution of the indanone derivatives.

So, the first object of the invention is process for the preparation of a compound of formula

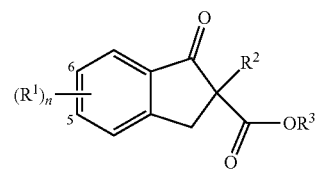

(I)

in the form of any one of its stereoisomers or a mixture thereof, and wherein n is an integer between 0 and 2, each $R^1$, independently from each other, represents a substituent of the aromatic ring and is a $C_{1-6}$ alkyl group, a $C_{2-6}$ alkenyl group or a $C_{1-6}$ alkoxy group; $R^2$ represents a $C_{1-3}$ alkyl group; and $R^3$ represents a hydrogen atom, a $C_{1-6}$ alkyl group or a $C_{2-6}$ alkenyl group;

comprising the cyclisation of a compound of the formula (II)

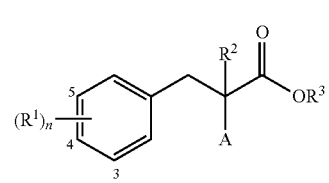

(II)

in the form of any one of its stereoisomers or a mixture thereof, and wherein n, $R^1$, $R^2$ and $R^3$ have the same meaning as defined in formula (I); and A represents a a C(O)OC(O)$R^4$ group, a C(O)Cl group or a COOH group wherein $R^4$ represents a $C_{1-6}$ alkyl group substituted by one or more chlorine or fluorine atoms;

in a presence of a Friedel-Crafts acylation reagent.

For the sake of clarity, by the expression "any one of its stereoisomers or a mixture thereof", or the similar, it is meant the normal meaning understood by a person skilled in the art, i.e. that the compound of formula (I) and (II) can be a pure enantiomer or a mixture of enantiomers. In other words, the compound of formula (I) and (II) may possess at least one stereocenter which can have two different stereochemistries (e.g. R or S). The compound of formula (I) and (II) may even be in the form of a pure enantiomer or in the form of a mixture of enantiomers. The compound of formula (I) and (II) may even be in the form of a pure diastereoisomer or in the form of a mixture of diastereoisomer when compound of formula (I) and (II) possess more than one stereocenter. The compound of formula (I) and (II) can be in a racemic form or scalemic form. Therefore, the compound of formula (I) and (II) can be one stereoisomers or in the form of a composition of matter comprising, or consisting of, various stereoisomers.

For the sake of clarity, by the expression "Friedel-Crafts acylation reagent", it is meant any reagent known by a person skilled in the art to perform the acylation of an aromatic ring through an electrophilic aromatic substitution. This type of conversion is very well known by a person skilled in the art and well documented in any handbook of organic chemistry.

The terms "alkyl" and "alkenyl" are understood as comprising branched and linear alkyl and alkenyl groups.

According to any embodiment of the invention, the cyclisation of compound of formula (II) may provide one compound of formula (I) or a mixture of two isomers depending on the position of the $R^1$ group(s) on the aromatic ring in the compound of formula (II). For example, two isomers can be obtained if there is only a substituent at position 3 of the aromatic ring of compound of formula (II). Both isomers can be converted further in the subsequent steps or can be separated. The person skilled in the art is well able to select the most suitable method to separate each isomer.

According to any embodiment of the invention, n may be 0 or 1 and particularly 1.

According to any embodiment of the invention, the compound of formula (I) may be of formula

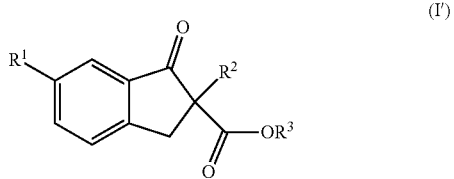

(I')

wherein each $R^1$, $R^2$ and $R^3$ have the same meaning as defined above.

According to any embodiment of the invention, the compound of formula (II) may be of formula

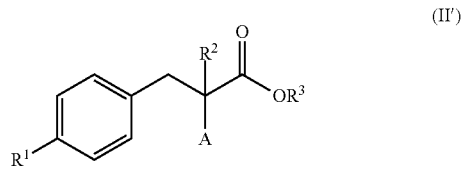

(II')

wherein each $R^1$, $R^2$, $R^3$ and A have the same meaning as defined above.

According to any embodiment of the invention, the compound of formula (II) or (II') may be obtained by the reaction between compound of formula (III)

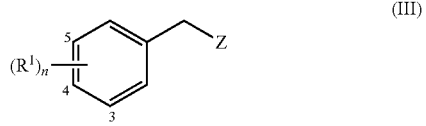

(III)

wherein Z represents a good leaving group such as an ether group, a perfluoroalkylsulfonate group, a tosylate group, a mesylate group or an halogen atom, in particular a chloride atom;

and dialkyl methyl malonate or 3-alkoxy-2-methyl-3-oxopropanoic acid. When the reaction is performed with dialkyl methyl malonate, a monohydrolyse and optionally a monochlorination or an acid anhydride formation step is needed to obtain respectively compound of formula (II) with A being COOH, a C(O)Cl group or C(O)OC(O)$R^4$ group. These reactions are generally known by a person skilled in the art and one particular embodiment is exemplified in the Examples.

According to a particular embodiment, when A represents a C(O)Cl group, said compound of formula (II) or (II') may be prepared in situ starting from the corresponding mono acid/mono ester; i.e. starting from compound of formula (II) or (II') wherein A is a COOH group.

According to a particular embodiment, when A represents a C(O)OC(O)$R^4$ group, said compound of formula (II) or (II') is prepared in situ starting from the corresponding mono acid/mono ester; i.e. starting from compound of formula (II) or (II') wherein A is a COOH group or from the acyl chloride/mono ester; i.e. starting from compound of formula (II) or (II') wherein A is a COCl group or from the anhydride/mono ester; i.e. starting from compound of formula (II'') as defined below wherein A is a C(O)OC(O)$R^5$ group wherein $R^5$ is a $C_{1-6}$ alkyl group, preferably $R^5$ is a methyl or ethyl group.

According to any embodiment of the invention, A may be a C(O)Cl group or a COOH group, in particular a COOH group.

According to any embodiment of the invention, $R^2$ may represent $C_{1-2}$ alkyl group. In particular, $R^2$ may represent a methyl group.

According to any embodiment of the invention, $R^3$ may represent a hydrogen atom, a $C_{1-5}$ alkyl group or a $C_{2-5}$ alkenyl group. In particular, $R^3$ may represent a $C_{1-3}$ alkyl group. In particular, $R^3$ may represent a methyl or an ethyl group.

According to any embodiment of the invention, $R^4$ may represent a $C_{1-4}$ alkyl group substituted by one, two or three chlorine or fluorine atoms. In particular, $R^4$ may represent a $C_{1-3}$ alkyl group substituted by one or three chlorine or fluorine atoms. In particular, $R^4$ may represent a $CCl_3$, $CF_3$ or $CH_2Cl$ group.

According to any embodiment of the invention, $R^1$ is a substituent of the aromatic ring, in particular, on position 5 and/or 6 of aromatic ring of compound of formula (I) or on position 3, 4 and/or 5 of aromatic ring of compound of formula (II). $R^1$ may represent, independently from each other, a $C_{1-4}$ alkyl group, a $C_{2-4}$ alkenyl group or a $C_{1-3}$ alkoxy group. In particular, $R^1$ may represent, independently from each other, a $C_{1-3}$ alkyl group or a $C_{2-3}$ alkenyl group. In particular, $R^1$ may represent, independently from each other, a methyl or an ethyl group. In particular, $R^1$ may be a methyl group.

According to any embodiment of the invention, the Friedel-Crafts acylation reagent may be an inorganic acid or a Lewis acid. According to a particular embodiment, suitable inorganic acid may include polyphosphoric acid, Eaton's reagent and perfluorinated ion-exchange resin.

For the sake of clarity, by the expression "Eaton's reagent", it is meant the normal meaning understood by a person skilled in the art, i.e. a mixture of $P_2O_5$ and methanesulfonic acid.

According to any embodiment of the invention, the Lewis acid is of formula M(Y)n wherein M is a metal selected from the group consisting of Al, B, Bi, Fe, Sn, Zn, In; n represents a integer between 2 and 4 and Y represents a halogen atom or a triflate or acetylacetone. According to a particular embodiment, suitable Lewis acid may include $BF_3 \cdot OEt_2$, $Bi(OTf)_3$, $AlCl_3$, $FeCl_2$, $FeCl_3$, $FeCl_3$ on silica gel 0.4 mmol/g, $FeCl_3 \cdot 6H_2O$, $InCl_3$, $SnCl_4$, $Zn(acac)_2$, $ZnBr_2$, $ZnCl_2$ and $ZnI_2$. In particular, the Lewis acid may be $BF_3 \cdot OEt_2$, $Bi(OTf)_3$, $FeCl_3$, $FeCl_3$ on silica gel 0.4 mmol/g, $FeCl_3 \cdot 6H_2O$, $InCl_3$, $SnCl_4$, $ZnCl_2$ and $ZnI_2$. In particular, the Lewis acid may be $BF_3 \cdot OEt_2$, $Bi(OTf)_3$ or $ZnI_2$.

According to a particular embodiment of the invention, when a Lewis acid is used, the invention process may be performed in the presence of an additive, said additive may be an acid anhydride, organic acid or phosphoryl chloride. In particular, examples of suitable acid anhydride may include trifluoroacetic anhydride, trichloroacetic anhydride, dichloroacetic anhydride, monochloroacetic anhydride and methanesulfonic anhydride. In particular, examples of suitable acid may include chloroacetic acid, trichloroacetic acid and trifluoroacetic acid.

According to a particular embodiment, when A represents a C(O)Cl group, the Friedel-Crafts acylation reagent may be a Lewis acid. In particular, suitable Lewis acid may be selected from the group consisting of $AlCl_3$, $FeCl_2$, $FeCl_3$, $FeCl_3$ on silica gel 0.4 mmol/g, $FeCl_3.6H_2O$, $InCl_3$, $SnCl_4$, $Zn(acac)_2$, $ZnBr_2$, $ZnCl_2$, $ZnI_2$ and a mixture thereof. In particular, suitable Lewis acid may be selected from the group consisting of $FeCl_3$, $FeCl_3$ on silica gel 0.4 mmol/g, $FeCl_3.6H_2O$, $InCl_3$, $SnCl_4$, $ZnI_2$ and a mixture thereof. In particular, suitable Lewis acid may be selected from the group consisting of $FeCl_3$ and $ZnI_2$ allowing the addition of a catalytic amount of Lewis Acid in the reaction medium; i.e. less than 0.51 equivalents.

According to a particular embodiment, when A represents a COOH group, the Friedel-Crafts acylation reagent may be an inorganic acid or a Lewis acid in combination with an acid anhydride or phosphoryl chloride. In particular, examples of suitable inorganic acids may be selected from the group consisting of polyphosphoric acid, Eaton's reagent or perfluorinated ion-exchange resin. In particular, examples of suitable Lewis acid may be selected from the group consisting of boron trifluoride diethyl etherate, $ZnCl_2$, $ZnI_2$ or bismuth(III) trifluoromethanesulfonate. In particular, examples of suitable acid anhydride may be selected from the group consisting of trifluoroacetic anhydride, methanesulfonic anhydride, trichloroacetic anhydride or 2-chloroacetic anhydride. In particular, examples of suitable combinations of Lewis acid and acid anhydride or phosphoryl chloride may be selected from the group consisting of boron trifluoride diethyl etherate with trifluoroacetic anhydride, boron trifluoride diethyl etherate with methanesulfonic anhydride, bismuth(III) trifluoromethanesulfonate with trifluoroacetic anhydride,. bismuth(III) trifluoromethanesulfonate with 2-chloroacetic anhydride, boron trifluoride diethyl etherate with 2-chloroacetic anhydride and $POCl_3$ with $ZnCl_2$.

According to a particular embodiment, when A represents $C(O)OC(O)R^4$ group, the Friedel-Crafts acylation reagent may be a Lewis acid. According to a particular embodiment, suitable Lewis acid may be selected from the group consisting of $Bi(OTf)_3$ and $BF_3·OEt_2$, preferably $Bi(OTf)_3$.

The inorganic acid can be added into the reaction medium of the invention's process in a large range of concentrations. As non-limiting examples, one can cite as inorganic acid concentration values those ranging from 0.5 to 10 equivalents, relative to the total amount of compound of formula (II). In particular, the inorganic acid concentration may be comprised between 1 to 4 equivalents. It goes without saying that the process works also with more inorganic acid. However the optimum concentration of inorganic acid will depend, as the person skilled in the art knows, on the nature of the latter, on the nature of the substrate, on the temperature and on the desired time of reaction.

The Lewis acid can be added into the reaction medium of the invention's process in a large range of concentrations. As non-limiting examples, one can cite as Lewis acid concentration values those ranging from 0.01 to 2.5 equivalents, relative to the total amount of compound of formula (II). In particular, the Lewis acid concentration may be comprised between 0.01 to 0.1 equivalent. It goes without saying that the process works also with more Lewis acid. However the optimum concentration of Lewis acid will depend, as the person skilled in the art knows, on the nature of the latter, on the nature of the substrate, on the temperature and on the desired time of reaction.

The additive can be added into the reaction medium of the invention's process in a large range of concentrations. As non-limiting examples, one can cite as additive concentration values those ranging from 1 to 10 equivalent, relative to the total amount of compound of formula (II). In particular, the additive concentration may be comprised between 1 to 5 equivalents. It goes without saying that the process works also with more additive. However the optimum concentration of additive will depend, as the person skilled in the art knows, on the nature of the latter, on the nature of the substrate, on the nature of the Lewis acid, on the temperature and on the desired time of reaction.

The temperature of the invention's process may be comprised between 22° C. and 150° C., more preferably in the range comprised between 60° C. and 110° C. Of course, a person skilled in the art is also able to select the preferred temperature as a function of the melting and boiling point of the starting and final products as well as the desired time of reaction or conversion.

The invention's process can be carried out in the presence or absence of a solvent. When a solvent is required or used for practical reasons, then any solvent current in Friedel-Crafts acylation reactions can be used for the purposes of the invention. In particular, examples of suitable solvents include $C_{6-10}$ aromatic solvents such as toluene or xylene; $C_{5-12}$ hydrocarbon solvents such as hexane or cyclohexane; $C_{4-8}$ ethers such as tetrahydrofuran or MTBE; $C_{4-10}$ esters such as ethyl acetate; $C_{1-2}$ chlorinated hydrocarbon, such as dichloromethane; $C_{2-6}$ primary or secondary alcohols, such as isopropanol or ethanol; $C_{2-6}$ polar solvents such as acetone; or mixtures thereof. In particular said solvent can be a solvent such as toluene or no solvent. The choice of the solvent is a function of the nature of the Friedel-Crafts reagent and the compound of formula (II), and the person skilled in the art is well able to select the solvent most convenient in each case to optimize the invention's process.

According to any embodiment of the invention, the compound of formula (I) may be further converted to compound of formula (IV)

(IV)

wherein each $R^1$ and n have the same meaning as defined above. Said compound of formula (IV) may be obtained via hydrogenolysis and hydrogenation of compound of formula (I). The conversion of compound of formula (I) into compound of formula (IV) is illustrated here-below in the experimental part.

The compound of formula (I) and/or (II) are, generally, novel compounds and present a number of advantages as explained above and shown in the Examples. Therefore, another object of the present invention is a compound of formula

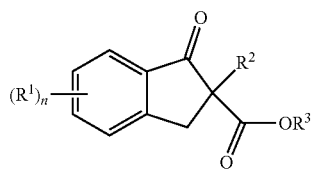

in the form of any one of its stereoisomers or a mixture thereof, and wherein n is an integer between 0 and 2, each $R^1$, independently from each other, represents a substituent of the aromatic ring and is a $C_{1-6}$ alkyl group, a $C_{2-6}$ alkenyl group or a $C_{1-6}$ alkoxy group; $R^2$ represents a $C_{1-3}$ alkyl group; and $R^3$ represents a hydrogen atom, a $C_{1-6}$ alkyl group or a $C_{2-6}$ alkenyl group; provided that 5-methoxy-2-methyl-1-oxo-2,3-dihydro-1H-indene-2-carboxylic acid, methyl 2-ethyl-5-methyl-1-oxo-2,3-dihydro-1H-indene-2-carboxylate, methyl 2-ethyl-6-methoxy-1-oxo-2,3-dihydro-1H-indene-2-carboxylate, ethyl 1-oxo-2-propyl-2,3-dihydro-1H-indene-2-carboxylate, methyl 2-ethyl-1-oxo-2,3-dihydro-1H-indene-2-carboxylate, methyl 2-isopropyl-1-oxo-2,3-dihydro-1H-indene-2-carboxylate, methyl 6-methoxy-1-oxo-2-propyl-2,3-dihydro-1H-indene-2-carboxylate, 2-methyl-1-oxo-2,3-dihydro-1H-indene-2-carboxylic acid, methyl 2-methyl-1-oxo-2,3-dihydro-1H-indene-2-carboxylate, ethyl 2-methyl-1-oxo-2,3-dihydro-1H-indene-2-carboxylate, allyl 2-methyl-1-oxo-2,3-dihydro-1H-indene-2-carboxylate, methyl 6-methoxy-2-methyl-1-oxo-2,3-dihydro-1H-indene-2-carboxylate, tert-butyl 2-methyl-1-oxo-2,3-dihydro-1H-indene-2-carboxylate, methyl 4-methoxy-2-methyl-1-oxo-2,3-dihydro-1H-indene-2-carboxylate, methyl 5,6-dimethoxy-2-methyl-1-oxo-2,3-dihydro-1H-indene-2-carboxylate, methyl 6-isobutyl-2-methyl-1-oxo-2,3-dihydro-1H-indene-2-carboxylate, ethyl 5-(tert-butyl)-2-methyl-1-oxo-2,3-dihydro-1H-indene-2-carboxylate, ethyl 2,5,7-trimethyl-1-oxo-2,3-dihydro-1H-indene-2-carboxylate and tert-butyl 5-methoxy-2-methyl-1-oxo-2,3-dihydro-1H-indene-2-carboxylate are excluded.

Another object of the present invention is a compound of formula

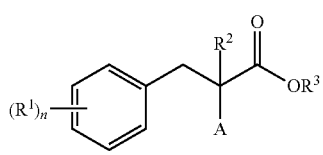

in the form of any one of its stereoisomers or a mixture thereof, and wherein n is an integer between 0 and 2, each $R^1$, independently from each other, represents a substituent of the aromatic ring and is a $C_{1-6}$ alkyl group, a $C_{2-6}$ alkenyl group or a $C_{1-6}$ alkoxy group; $R^2$ represents a $C_{1-3}$ alkyl group; $R^3$ represents a hydrogen atom, a $C_{1-6}$ alkyl group or a $C_{2-6}$ alkenyl group and A represents a C(O)Cl group; a C(O)OC(O)$R^5$ group, and $R^5$ represents a $C_{1-6}$ alkyl group provided that ethyl 3-chloro-2-(4-methoxy-3-methylbenzyl)-2-methyl-3-oxopropanoate is excluded.

Typical manners to execute the invention's process are reported herein below in the examples.

EXAMPLES

The invention will now be described in further detail by way of the following examples, wherein the abbreviations have the usual meaning in the art, the temperatures are indicated in degrees centigrade (° C.). NMR spectra were acquired using either a Bruker Avance II Ultrashield 400 plus operating at 400 MHz, ($^1$H) and 100 MHz ($^{13}$C) or a Bruker Avance III 500 operating at 500 MHz ($^1$H) and 125 MHz ($^{13}$C) or a Bruker Avance III 600 cryoprobe operating at 600 MHz ($^1$H) and 150 MHz ($^{13}$C). Spectra were internally referenced relative to tetramethyl silane 0.0 ppm. $^1$H NMR signal shifts are expressed in δ ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}$C NMR data are expressed in chemical shift δ ppm and hybridization from DEPT 90 and DEPT 135 experiments, C, quaternary; CH, methine; CH$_2$, methylene; CH$_3$, methyl.

Example 1

Preparation of Compound of Formula (I) Starting from Compound of Formula (II) with A Being a COOH Group a) Preparation of 3-ethoxy-2-methyl-2-(4-methylbenzyl)-3-oxopropanoic Acid A 50 ml round bottomed flask was charged with sodium hydroxide (7.55 ml, 7.55 mmol). The solution was cooled at 0° C. Diethyl 2-methyl-2-(4-methylbenzyl)malonate (2 g, 7.19 mmol) was dissolved with ethanol (20 ml, 7.19 mmol) and added dropwise over 5 min. The mixture was stirred at 0° C. for 5 min then warmed at RT. After 22 h, the mixture was poured over water and extracted 2× with ether. The water was acidified with hydrochloric acid (0.65 ml, 7.92 mmol). The aqueous phase was extracted 2× with ether, washed 1× with water and 2× with brine, dried with Na$_2$SO$_4$, filtered and concentrated to provide monoacid (1.58 g, 85%) as a clear oil. A sample of the desired product was treated with MSTFA and analyzed by GC.

$^1$H NMR (CDCl$_3$, 500 MHz) δ 7.07; (d, J=8.0 Hz, 2H), 7.03; (d, J=8.0 Hz, 2H), 4.22; (q, J=6.1 Hz, 2H), 3.25; (d, J=13.7 Hz, 1H), 3.17; (d, J=13.7 Hz, 1H), 2.31; (s, 3H), 1.40; (s, 3H), 1.28; (t, J=13.7 Hz, 3H).

$^{13}$C NMR (125 MHz, CDCl$_3$): δ 14.0; (q), 20.0; (q), 21.1; (q), 41.1; (t), 54.9; (s), 61.8; (t), 129.0; (d), 130.0; (d), 132.6; (s), 136.7; (s), 172.2; (s), 177.2; (s).

b) Preparation of Ethyl 2,6-dimethyl-1-oxo-2,3-dihydro-1H-indene-2-carboxylate

A flask equipped with a mechanical stirring was charged with polyphosphoric acid (29.0 g, 121 mmol). It was heat at 70° C. The 3-ethoxy-2-methyl-2-(4-methylbenzyl)-3-oxopropanoic acid (10 g, 40 mmol) was added by small portions over 10 mn. After 3 h30, ice cubes were added to the mixture and then ether was added. It was then extracted with ether, washed 1× with water, 1× with NaHCO$_3$ and 2× with brine, dried with Na$_2$SO$_4$, filtered, concentrated and distillated by bulb-to bulb distillation pressure=0.2 mbar/T°=140° C. to provide ethyl 2,6-dimethyl-1-oxo-2,3-dihydro-1H-indene-2-carboxylate (7.90 g, 34 mmol, 85%).

$^1$H NMR (CDCl$_3$, 500 MHz) δ 7.59; (s, 1H), 7.45; (d, J=6.5 Hz, 1H), 7.36; (d, J=6.5 Hz, 1H), 4.14; (q, J=6.0 Hz, 2H), 3.65; (d, J=14.1 Hz, 1H), 2.94; (d, J=14.1 Hz, 1H), 2.41; (s, 3H), 1.50; (s, 3H), 1.19; (t, J=6.0 Hz, 3H).

$^{13}$C NMR (90 MHz, CDCl$_3$): δ 14.0; (q), 21.1; (q), 39.8; (t), 56.3; (s), 61.4; (t), 124.8; (d), 126.2; (d), 134.9; (s), 136.6; (d), 137.8; (s), 150.0; (s), 172.1; (s), 203.6; (s).

Example 2

Preparation of Compound of Formula (I) Starting from Compound of Formula (II) with A Being a COOH Group in Different Conditions In a flask under $N_2$ was charged with 3-ethoxy-2-methyl-3-oxo-2-(p-tolylmethyl)propanoic acid as prepared in example 1 a) (10 g, 39.9 mmol) in the appropriate solvent (250 mL). Reagents A and reagent B were added. The solution was stirred at the indicated temperature for the indicated time. Then the mixture was poured in 5 ml $H_2O$ and stirred 5 mn at RT. $K_2CO_3$ 20% was added until pH=9 It was then extracted with ether, washed 1× with water, 2× with brine. It was dried with $Na_2SO_4$, filtered and concentrated. The GC yields of ethyl 2,6-dimethyl-1-oxo-2,3-dihydro-1H-indene-2-carboxylate (i.e. compound of formula (I)) are reported in table 1.

TABLE 1

Preparation of ethyl 2,6-dimethyl-1-oxo-2,3-dihydro-1H-indene-2-carboxylate using different conditions

| Reagents A | Eq. | Reagents B | Eq. | Solvent | T [° C.] | Time [h] | Yield [%] |
|---|---|---|---|---|---|---|---|
| $MeSO_3H$ | 1.4 | $P_2O_5$ | 0.3 | heptane | 100 | 2 h 30 | 65 |
| $BF_3 \cdot OEt_2$ | 0.18 | TFAA | 2 | none | 40 | 2 h | 87 |
| $BF_3 \cdot OEt_2$ | 0.18 | $(MeSO_2)_2O$ | 2 | none | 40-80 | 2 h | 87 |
| $Bi(OTf)_3$ | 0.1 | $(CCl_3CO)_2O$ | 2 | PhMe | 70 | 1 h | 93 |
| $Bi(OTf)_3$ | 0.1 | $(ClCH_2CO)_2O$ | 1.2 | none | 70-120 | 1 h 30 | 97 |
| $BF_3 \cdot OEt_2$ | 0.05 | $(ClCH_2CO)_2O$ | 1.2 | none | 120 | 2 h | 80 |
| Eaton's | 3 | / | / | none | 70 | 2 h 30 | 81 |
| $POCl_3$ | 9.7 | $ZnCl_2$ | 2.5 | none | 80 | 2 h | 84 |

Example 3

Preparation of Compound of Formula (I) Starting from Compound of Formula (II) with A Being a COCl Group a) Preparation of Ethyl 3-chloro-2-methyl-2-(4-methylbenzyl)-3-oxopropanoate A 500 ml round bottomed flask was charged with the 3-ethoxy-2-methyl-3-oxo-2-(p-tolylmethyl)propanoic acid (10 g, 39.9 mmol) in DCM (250 mL). Thionyl chloride (14.49 mL, 199.8 mmol) was added dropwise over 3 min. The mixture was refluxed. After 4 h30, the mixture was concentrated to give ethyl 3-chloro-2-methyl-2-(4-methylbenzyl)-3-oxopropanoate (10.3 g, 95.7%).

$^1$H NMR (CDCl3, 500 MHz) 57.06; (d, J=7.9 Hz, 2H), 7.03; (d, J=7.9 Hz, 2H), 4.26; (q, J=7.2 Hz, 2H), 3.27; (s, 2H), 2.31; (s, 3H), 1.43; (s, 3H), 1.30; (t, J=7.2 Hz, 3H);

$^{13}$C NMR (125 MHz, $CDCl_3$): δ 13.8; (q), 19.9; (q), 21.1; (q), 40.8; (t), 62.3; (t), 64.9; (s), 129.2 (d), 130.0 (d), 131.5 (s), 137.1; (s), 169.4; (s), 173.3; (s);

b) Preparation of Ethyl 2,6-dimethyl-1-oxo-indane-2-carboxylate

A 100 ml round bottomed flask was charged with ethyl 3-chloro-2-methyl-2-(4-methylbenzyl)-3-oxopropanoate (5.32 g, 19.8 mmol) and toluene (50 mL). The mixture was stirred at RT and iron (III) chloride anhydrous (0.21 g, 1.3 mmol) was added. The mixture was then refluxed. The mixture was cooled at RT.

The mixture was poured over water/ice and extracted with ether. It was washed 1× with water, 1× with sodium carbonate and 2× with brine, dried with sodium sulfate, filtered, concentrated and purified by bulb-to-bulb distillation (pressure=0.1 mbar/T=160° C.) to provide ethyl 2,6-dimethyl-1-oxo-indane-2-carboxylate (4.16 g, 17.9 mmol, 90.4%).

$^1$H NMR (CDCl3, 400 MHz) δ 7.59; (s, 1H), 7.45; (d, J=6.5 Hz, 1H), 7.36; (d, J=6.5 Hz, 1H), 4.14; (q, J=6.0 Hz, 2H), 3.65; (d, J=14.1 Hz, 1H), 2.94; (d, J=14.1 Hz, 1H), 2.41; (s, 3H), 1.50; (s, 3H), 1.19; (t, J=6.0 Hz, 3H).

$^{13}$C NMR (90 MHz, $CDCl_3$) δ 14.0; (q), 21.1; (q), 39.8; (t), 56.3; (s), 61.4; (t), 124.8; (d), 126.2; (d), 134.9; (s), 136.6; (d), 137.8; (s), 150.0; (s), 172.1; (s), 203.6; (s).

Example 4

Preparation of Compound of Formula (I) Starting from Compound of Formula (II) with A Being a COOH Group a) Preparation of 3-methoxy-2-methyl-2-(4-methylbenzyl)-3-oxopropanoic Acid A 750 ml round bottomed flask under $N_2$ was charged with 3-methoxy-2-methyl-2-(4-methylbenzyl)-3-oxopropanoic acid (161.8 g, 685 mmol) in MeOH (42 mL). Add slowly in 1 h (62 ml/h, 1 ml/min) at −10° C. sodium hydroxide (61.8 ml, 616 mmol) solution 30% and stirred for a night at −10° C. Part of the solvent (153 g MeOH dist, trap 20 g) was distilled under vaccum (Tmax=40-50, DeltaT=30° C., 150-20 mbar). Add water (210 ml, 1.16E+04 mmol) to the mixture. Wash 3× the mixture with cyclohexane (96 ml, 890 mmol) at RT. At 40° C. sulfuric acid (36.5 ml, 342 mmol) (9.4 ml/h) 50% in water was added to the solution until pH=3. The water was separated from the oil phase. The water phase was extracted twice with ethyl acetate (101 ml, 1027 mmol) at RT. The combined organic layers were dried and then the solvent was removed by evaporation to give a colorless liquid (62.5% yield):

$^1$H RMN (CDCl3) 1.51; (s, 3H), 2.30; (s, 3H), 2.95; (s, 1H), 3.65; (s, 1H), 3.67; (s, 3H), 7.36; (d, J=7 Hz, 1H), 7.45; (d, J=7 Hz, 1H), 7.58; (s, 1H).

$^{13}$C NMR (150 MHz, $CDCl_3$): 21.1; (q), 21.1; (q), 39.7; (t), 52.6; (q), 56.3; (s), 124.8; (d), 126.2; (d), 134.9; (s), 136.7; (d), 137.9; (s), 150.0; (s), 172.6; (s), 203.5; (s).

b) Preparation of Methyl 2,6-dimethyl-1-oxo-2,3-dihydro-1H-indene-2-carboxylate

A flask equipped with a mechanical stirring was charged with polyphosphoric acid (308 g, 1282 mmol). It was heat at 70° C. 3-methoxy-2-methyl-2-(4-methylbenzyl)-3-oxopropanoic acid (101 g, 427 mmol) was added by small portions over 10 min. After 1 h30 at 70-90° C. water was added to the mixture and it was then extracted with ethyl acetate, washed 1× with $NaHCO_3$ and 1× with $NH_4Cl$, dried with $Na_2SO_4$, filtered and concentrated (Crude=70 g). The product was recrystallized in ether (63% yield).

$^1$H RMN (CDCl3) 1.51; (s, 3H), 2.30; (s, 3H), 2.95; (s, 1H), 3.65; (s, 1H), 3.67; (s, 3H), 7.36; (d, J=7 Hz, 1H), 7.45; (d, J=7 Hz, 1H), 7.58; (s, 1H).

$^{13}$C NMR (150 MHz, CDCl$_3$): 21.1; (q), 21.1; (q), 39.7; (t), 52.6; (q), 56.3; (s), 124.8; (d), 126.2; (d), 134.9; (s), 136.7; (d), 137.9; (s), 150.0; (s), 172.6; (s), 203.5; (s).

Example 5

Preparation of Ethyl 2,5-dimethyl-2,3-dihydro-1H-indene-2-carboxylate Starting from Ethyl 2,6-dimethyl-1-oxo-2,3-dihydro-1H-indene-2-carboxylate Ethyl 2,6-dimethyl-1-oxo-2,3-dihydro-1H-indene-2-carboxylate (1 eq.), Pd/C (0.14-0.19 mol. % Pd relative to starting material, egg-shell type catalyst), acetic acid (100 wt. % respect to starting material) and acetic anhydride (26 wt. % i.e. 0.6 eq. respect to starting material) were loaded altogether in an autoclave equipped with a mechanical stirring device, pressure and internal temperature sensors and a heating/cooling system for internal temperature regulation. Sealed autoclave was then purged under stirring with nitrogen (3 times 5 bars) and hydrogen (3 times 5 bars) before being pressurized to required hydrogen pressure (28 bars) via an hydrogen tank equipped with a way out pressure regulator and also an internal pressure sensor to follow and determine hydrogen consumption. In addition to hydrogen consumption, hydrogenation reaction was followed by GC analysis of samples collected all along the reaction. Reaction mixture was initially heated to 60° C. and maintained to this temperature until complete starting material disappearance. Additional acetic anhydride (39.5 wt. % i.e. 0.9 eq. respect to starting material) was then added to the reaction mixture at 60° C. under pressure using some adequate pump equipment. Reaction mixture was then progressively further heated from 60° C. to 140° C. At the end of the reaction (complete disappearance of both starting material and intermediates), autoclave was cooled down to 25° C., carefully vented, purged with nitrogen and reaction mixture was transferred to some filtration equipment for heterogeneous catalyst removal. After concentration of light compounds under vacuum, crude reaction mixture was purified by fractional distillation to afford desired ethyl 2,5-dimethyl-2,3-dihydro-1H-indene-2-carboxylate in 90% molar yield.

$^1$H NMR (500 MHz, C$_2$DCl$_2$): δ (ppm) 1.23; (t, J=7.1 Hz, 3H, CH$_3$), 1.32; (s, 3H, CH$_3$), 2.29; (s, 3H, CH$_3$), 2.74; (d, J=15.6 Hz, 2H, CH$_2$), 3.39; (d, J=15.8 Hz, 1H, CH$_2$), 3.41; (d, J=15.8 Hz, 1H, CH$_2$), 4.12; (q, J=7.1 Hz, 3H, CH$_3$), 6.94; (d, J=7.5 Hz, 1H, CH), 6.98; (s, 1H, CH), 7.04; (d, J=7.5 Hz, 1H, CH).

$^{13}$C NMR (125 MHz, CD$_2$Cl$_2$) δ (ppm) 14.4; (CH$_3$), 21.4; (CH$_3$), 25.2; (CH$_3$), 43.9; (CH$_2$), 44.2; (CH$_2$), 50.0; (C), 60.9; (CH$_3$), 124.6; (CH), 125.6; (CH), 127.6 (CH), 136.5; (C), 138.8; (C), 142.0; (C), 177.7; (CO ester).

Example 6

Preparation of (2,5-dimethyl-2,3-dihydro-1H-inden-2-yl)methanol starting from ethyl 2,5-dimethyl-2,3-dihydro-1H-indene-2-carboxylate Ethyl 2,5-dimethyl-2,3-dihydro-1H-indene-2-carboxylate, ruthenium complex [RuCl$_2$((E)-N-(2-(diphenylphosphino)benzyl)-1-(6-((diphenylphoshino)methyl)pyridine-2-yl)methanimine)](0.0113-0.0173 wt. % i.e. 0.00333-0.005 mol. % respect to starting material) and 21 wt. % sodium ethoxide solution in ethanol (7.4 wt. % i.e. 5 mol. % respect to starting material) were loaded altogether in an autoclave equipped with a mechanical stirring device, pressure and internal temperature sensors and a heating/cooling system for internal temperature regulation. Sealed autoclave was then purged under stirring with nitrogen (3 times 5 bars) and hydrogen (3 times 5 bars) before being pressurized to required hydrogen pressure (50 bars) via an hydrogen tank equipped with a way out pressure regulator and also an internal pressure sensor to follow and determine hydrogen consumption. Reaction mixture was then heated to required temperature (100° C.) and hydrogen pressure into the autoclave was maintained to the desired value during the whole reaction. Upon reaction completion also determined by GC analysis with complete disappearance of both starting material and mixed ester coming from transesterification reaction with product, autoclave was then cooled down to 25° C. It was then depressurized and purged with nitrogen (3 times 5 bars) and reaction mixture was then transferred to a round-bottomed flask and lights compounds were removed under vacuum. Crude product was then flash distilled under high vacuum in order to remove ruthenium catalyst and salts before being purified by fractional distillation for careful removal of lights compounds to afford desired (2,5-dimethyl-2,3-dihydro-1H-inden-2-yl)methanol meeting olfactive requirements in 98% molar yield.

(2,5-dimethyl-2,3-dihydro-1H-inden-2-yl)methanol was characterized by $^1$H and $^{13}$C NMR, data obtained meeting those from some reference in literature; i.e. B. Winter, S. Gallo-Fluckiger, Helv. Chim. Acta 2005, 88(12), 3118-3127.

(2,5-dimethyl-2,3-dihydro-1H-inden-2-yl)methanol was obtained in 75% overall yield starting from Diethyl 2-methyl-2-(4-methylbenzyl)malonate following the sequence reported in examples 1, 5 and 6 Whereas, (2,5-dimethyl-2,3-dihydro-1H-inden-2-yl)methanol was obtained with a 67% overall yield starting from 1-(p-tolyl)propan-1-one as reported in WO2016113151. The invention's process allows producing (2,5-dimethyl-2,3-dihydro-1H-inden-2-yl)methanol derivatives with an improved yield.

The invention claimed is:
1. A process for the preparation of a compound of formula

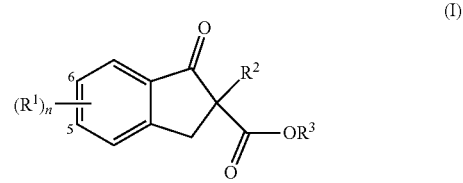

in the form of any one of its stereoisomers or a mixture thereof, and wherein n is an integer between 0 and 2, each R$^1$, independently from each other, represents a substituent of the aromatic ring and is a C$_{1-6}$ alkyl group, a C$_{2-6}$ alkenyl group or a C$_{1-6}$ alkoxy group; R$^2$ represents a C$_{1-3}$ alkyl group; and R$^3$ represents a hydrogen atom, a C$_{1-6}$ alkyl group or a C$_{2-6}$ alkenyl group;

comprising the cyclisation of a compound of the formula (II)

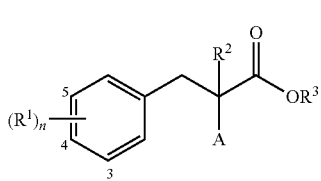

(II)

in the form of any one of its stereoisomers or a mixture thereof, and wherein n, $R^1$, $R^2$ and $R^3$ have the same meaning as defined in formula (I); and A represents a C(O)OC(O)$R^4$ group, a C(O)Cl group or a COOH group wherein $R^4$ represents a $C_{1-6}$ alkyl group substituted by one or more chlorine or fluorine atoms;

in a presence of a Friedel-Crafts acylation reagent.

2. The process according to claim 1, wherein the compound of formula (I) is of formula

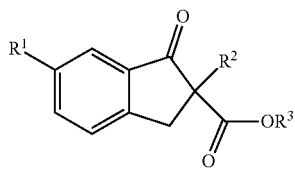

(I')

wherein each $R^1$, $R^2$ and $R^3$ have the same meaning as defined in claim 1;

and said compound of formula (II) is of formula

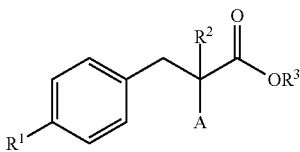

(II')

wherein each $R^1$, $R^2$, $R^3$ and A have the same meaning as defined in claim 1.

3. The process according to claim 1, wherein A is a COOH group.

4. The process according to claim 1, wherein $R^2$ is a methyl group.

5. The process according to claim 1, wherein $R^3$ represents a $C_{1-3}$ alkyl group.

6. The process according to claim 1, wherein $R^1$, independently from each other, is a $C_{1-4}$ alkyl group.

7. The process according to claim 1, wherein the Friedel-Crafts acylation reagent is an inorganic acid or a Lewis acid.

8. The process according to claim 7, wherein the inorganic acid is selected from the group consisting of polyphosphoric acid, Eaton's reagent, and perfluorinated ion-exchange resin.

9. The process according to claim 7, wherein the Lewis acid is of formula M(Y)n, wherein M is a metal selected from the group consisting of Al, B, Bi, Fe, Sn, Zn, In, n represents an integer between 2 and 4, and Y represents a halogen atom or a triflate or acetylacetone.

10. The process according to claim 9, wherein the Lewis acid is selected from the group consisting of BF$_3$·OEt$_2$, Bi(OTf)$_3$, AlCl$_3$, FeCl$_2$, FeCl$_3$, FeCl$_3$ on silica gel 0.4 mmol/g, FeCl$_3$·6H$_2$O, InCl$_3$, SnCl$_4$, Zn(acac)$_2$, ZnBr$_2$, ZnCl$_2$ and ZnI$_2$.

11. The process according to claim 1, wherein the cyclisation is performed in a presence of a Lewis acid and an acid anhydride, an organic acid or phosphoryl chloride.

12. The process according to claim 11, wherein the acid anhydride is selected from the group consisting of trifluoroacetic anhydride, trichloroacetic anhydride, dichloroacetic anhydride, monochloroacetic anhydride and methanesulfonic anhydride.

13. The process according to claim 1, further comprising the step of converting compound of formula (I) to compound of formula (IV)

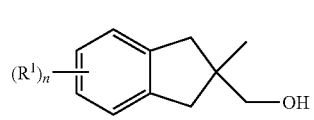

(IV)

wherein each $R^1$ and n have the same meaning as defined in claim 1.

14. A compound of formula

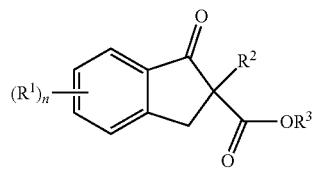

(I)

in the form of any one of its stereoisomers or a mixture thereof, and wherein n is an integer between 0 and 2, each $R^1$, independently from each other, represents a substituent of the aromatic ring and is a $C_{1-6}$ alkyl group, a $C_{2-6}$ alkenyl group or a $C_{1-6}$ alkoxy group; $R^2$ represents a $C_{1-3}$ alkyl group; and $R^3$ represents a hydrogen atom, a $C_{1-6}$ alkyl group or a $C_{2-6}$ alkenyl group; provided that 5-methoxy-2-methyl-1-oxo-2,3-dihydro-1H-indene-2-carboxylic acid, methyl 2-ethyl-5-methyl-1-oxo-2,3-dihydro-1H-indene-2-carboxylate, methyl 2-ethyl-6-methoxy-1-oxo-2,3-dihydro-1H-indene-2-carboxylate, ethyl 1-oxo-2-propyl-2,3-dihydro-1H-indene-2-carboxylate, methyl 2-ethyl-1-oxo-2,3-dihydro-1H-indene-2-carboxylate, methyl 2-isopropyl-1-oxo-2,3-dihydro-1H-indene-2-carboxylate, methyl 6-methoxy-1-oxo-2-propyl-2,3-dihydro-1H-indene-2-carboxylate, 2-methyl-1-oxo-2,3-dihydro-1H-indene-2-carboxylic acid, methyl 2-methyl-1-oxo-2,3-dihydro-1H-indene-2-carboxylate, ethyl 2-methyl-1-oxo-2,3-dihydro-1H-indene-2-carboxylate, allyl 2-methyl-1-oxo-2, 3-dihydro-1H-indene-2-carboxylate, methyl 6-methoxy-2-methyl-1-oxo-2,3-dihydro-1H-indene-2-carboxylate, tert-butyl 2-methyl-1-oxo-2,3-dihydro-1H-indene-2-carboxylate, methyl 4-methoxy-2-methyl-1-oxo-2,3-dihydro-1H-indene-2-carboxylate, methyl 5,6-dimethoxy-2-methyl-1-oxo-2,3-dihydro-1H-indene-2-carboxylate, methyl 6-isobutyl-2-methyl-1-oxo-2,3-dihydro-1H-indene-2-carboxylate, ethyl 5-(tert-butyl)-2-methyl-1-oxo-2,3-dihydro-1H-indene-2-carboxylate, ethyl 2,5,7-trimethyl-1-oxo-2,3-dihydro-1H-indene-2-carboxylate and tert-butyl 5-methoxy-2-methyl-1-oxo-2,3-dihydro-1H-indene-2-carboxylate are excluded.

15. A compound of formula

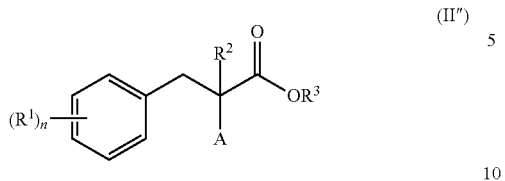

(II″)

in the form of any one of its stereoisomers or a mixture thereof, and wherein n is an integer between 0 and 2, each $R^1$, independently from each other, represents a substituent of the aromatic ring and is a $C_{1-6}$ alkyl group, a $C_{2-6}$ alkenyl group or a $C_{1-6}$ alkoxy group; $R^2$ represents a $C_{1-3}$ alkyl group; $R^3$ represents a hydrogen atom, a $C_{1-6}$ alkyl group or a $C_{2-6}$ alkenyl group and A represents a C(O)Cl group; a $C(O)OC(O)R^5$ group, and $R^5$ represents a $C_{1-6}$ alkyl group provided that ethyl 3-chloro-2-(4-m ethoxy-3-methylbenzyl)-2-methyl-3-oxopropanoate is excluded.

* * * * *